United States Patent [19]
Umino et al.

[11] Patent Number: 5,831,113
[45] Date of Patent: Nov. 3, 1998

[54] PROCESS FOR PRODUCING A CARBONIC ACID DIESTER

[75] Inventors: Hiroshi Umino, Yokohama; Kozo Imura, Handa; Takeshi Koyama, Yokohama, all of Japan

[73] Assignee: JGC Corporation, Tokyo, Japan

[21] Appl. No.: 896,228

[22] Filed: Jul. 17, 1997

[30] Foreign Application Priority Data

Jul. 22, 1996 [JP] Japan .................................. 8-192318
Mar. 12, 1997 [JP] Japan .................................. 9-057707

[51] Int. Cl.$^6$ .................................................. C07C 68/00
[52] U.S. Cl. ........................ 558/260; 558/270; 558/274; 558/275; 558/277
[58] Field of Search .................................. 558/260, 270, 558/274, 275, 277

[56] References Cited

U.S. PATENT DOCUMENTS 5,536,864  7/1996  Paret et al. .............................. 558/277

OTHER PUBLICATIONS

Japanese Abstract No. 54024827, 1979.
Japanese Abstract No. 50040528, 1975.
Japanese Abstract No. 86008816, 1986.
Japanese Abstract No. 62081356, 1987.
Japanese Abstract No. 1287062, 1989.
Japanese Abstract No. 63503460, 1988.

*Primary Examiner*—Michael G. Ambrose
*Attorney, Agent, or Firm*—Webb Ziesenheim Bruening Logsdon Orkin & Hanson, P.C.

[57] ABSTRACT

A process for producing a carbonic acid diester, which comprises carrying out a reaction in a vapor phase of an alcohol, carbon monoxide and oxygen in the presence of a catalyst in a fluidized-bed reactor so that an oxidative carbonylation of the alcohol occurs, thereby obtaining a carbonic acid diester, wherein a heat of reaction is removed by the latent heat of vaporization of the alcohol as a raw material. In the process, for example, either at least part of the alcohol may be directly fed in liquid phase into the fluidized bed or cooling pipes are disposed in the fluidized bed and at least part of the alcohol is introduced in liquid phase into the cooling pipes as a heat transfer medium so that the liquid alcohol is vaporized and fed into the fluidized-bed reactor. Carbon monoxide may be introduced together with the liquid alcohol into the cooling pipes. A process of high energy efficiency realizing an effective utilization of a heat of reaction and an apparatus there for are provided in the production of a carbonic acid diester in a vapor phase with the use of a fluidized-bed reactor.

7 Claims, 5 Drawing Sheets

PROCESS FOR PRODUCING A CARBONIC ACID DIESTER

FIELD OF THE INVENTION

The present invention relates to a process for producing a carbonic acid diester, in which the carbonic acid diester is produced in a vapor phase with the use of a fluidized-bed reactor, and an apparatus therefor.

BACKGROUND OF THE INVENTION

Carbonic acid diester such as dimethyl carbonate are attracting attention as a raw material substituted for phosgene or dimethyl sulfate in the production of isocyanates, polycarbonates and various drugs and agricultural chemicals. Further, the use thereof as an additive to automobile fuel is being considered.

Carbonic acid diester has long been produced by reacting phosgene with an alcohol. However, the use of phosgene has drawbacks in that phosgene is highly toxic and that the reaction forms hydrochloric acid as a by-product, which causes corrosion of the apparatus. Therefore, processes for producing carbonic acid diester without the use of phosgene have been developed and are now being executed on industrial scales.

For example, Japanese Patent Laid-open Publication No. 54(1979)-24827 discloses a process for producing a carbonic acid diester, in which an alcohol, carbon monoxide and oxygen react in the liquid phase in the presence of a copper halide catalyst. Furthermore, Japanese Patent Laid-open Publication No. 50(1975)-40528, Japanese Patent Publication No. 61(1986)-8816 and Japanese Patent Laid-open Publication Nos. 62(1987)-81356 and 1(1989)-287062 disclose processes for producing the carbonic acid diester in liquid phase, in which copper and palladium halides are used as catalytic components.

Although having the advantage of using no phosgene, the above processes for producing carbonic acid diester in the liquid phase have drawbacks in that, (1) the reaction apparatus is likely to corrode by the action of a halide catalyst which is used as a solution (2), the catalyst activity is deteriorated rapidly by the water formed during the reaction and (3)it is difficult to separate the catalyst dissolved in the reaction product. In particular, it is requisite that the reaction apparatus is constructed of a corrosion resistant high-quality material to thereby prevent the corrosion of the apparatus and any disaster attributed to the corrosion. This inevitably causes the construction cost of the apparatus to be extremely high.

Processes for producing carbonic acid diester by vapor phase reaction have been proposed as substitutes for the liquid phase processes (for example, Published Japanese Translation of PCT Patent Applications from Other States, No. 63(1988)-503460, Japanese Patent Laid-open Publication No. 4(1992)-89458 and International Application Publication Wo 90/15791).

In the vapor phase processes disclosed in these publications, vaporized alcohol, carbon monoxide and oxygen react in the vapor phase in the presence of a catalyst, and the resultant gaseous reaction product is withdrawn from the reactor. The withdrawn gas is cooled to thereby separate it into a condensed liquid and a noncondensable gas and the carbonic acid diester is separated from the liquid. These vapor phase processes are substantially free from the above drawbacks of the liquid phase processes.

Apart from the above, the oxidative carbonylation of an alcohol is an exothermic reaction. The heat of reaction must be removed for maintaining an appropriate reaction temperature. For example, the calorific values are about 71 kcal/mol in both of the following reactions in which carbonic acid diesters are prepared from methanol and ethanol:

$2CH_3OH+CO+1/2O_2 \rightarrow (CH_3O)_2CO+H_2O$, and $2C_2H_5OH+CO+1/2O_2 \rightarrow (C_2H_5O)_2CO+H_2O$.

When a catalyst consists of, for example, a copper oxychloride supported on an active carbon, the above oxidative carbonylation of an alcohol in the vapor phase is conducted at a temperature as relatively low as about 130° to 1700° C.

When it is attempted to synthesize a carbonic acid diester by the use of a fixed-bed reactor, hot spots are likely to occur because the reaction is highly exothermic, so that the dangers of decrease of reaction selectivity, runaway of reaction and catalyst deactivation are increased.

By contrast, the heat of reaction can be removed much more easily in a fluidized-bed reactor than in the fixed-bed reactor, so that the temperature can be controlled without the occurrence of hot spots.

In the above vapor phase reaction in the fluidized-bed reactor, generally, cooling pipes are inserted in the fluidized bed so as to effect heat removal and water is generally used as the heat transfer medium. For example, International Application Publication WO 95/21692 discloses a fluidized-bed reactor for vapor-phase exothermic reaction which is provided with cooling pipes capable of feeding a cooling medium at a steady rate and cooling pipes capable of feeding a cooling medium at a variable rate. In the publication, water is mentioned as the cooling medium fed at a steady rate and steam is mentioned as the cooling medium fed at a variable rate.

If steam obtained by the vaporization resulting from the removal of the heat of reaction generated in the fluidized bed can be used as, for example, a heat source for a reboiler of a distillation column, effective utilization of the heat of reaction would be attained. When the difference between the reaction temperature and the temperature of the heat transfer medium flowing through the cooling pipes are large, the removal of the heat of reaction would be easy.

In the oxidative carbonylation conducted at relatively low temperatures, the difference between the reaction temperature and the temperature of steam available as a heat source (for example, about 125° C. with respect to reboiler heat source) is so small that the number of cooling pipes must be increased to thereby enlarge the heat-transfer area in order to obtain the steam of the above temperature.

However, the number of cooling pipes which can be inserted in a fluidized bed of a given volume is so limited that it is likely that the heat-transfer area required for the removal of heat cannot be satisfactorily secured. Further, when the removal of heat is attempted by increasing the difference between the reaction temperature and the temperature of heat transfer medium under the condition of the limited number of cooling pipes, only low-temperature steam or water can be obtained, which has little value.

On the other hand, the attempt to increase the heat-transfer area leads to an unnecessary expansion of the volume of the fluidized bed.

Therefore, there has been a demand for the development of a process capable of producing a carbonic acid diester in high energy efficiency with the effective utilization of the heat of reaction in the vapor-phase oxidative carbonylation of an alcohol which is conducted at relatively low temperatures.

OBJECT OF THE INVENTION

The present invention has been made taking the above prior art into account. An object of the present invention is to provide a vapor-phase process for producing a carbonic acid diester by means of a fluidized-bed reactor wherein the carbonic acid diester can be produced in high energy efficiency with the effective utilization of the heat of reaction, and an another object of the present invention is to provide an apparatus for producing a carbonic acid diester which is suitable for the above process.

SUMMARY OF THE INVENTION

The process for producing a carbonic acid diester according to the present invention comprises carrying out a reaction in a vapor phase of an alcohol, carbon monoxide and oxygen in the presence of a catalyst in a fluidized-bed reactor so that an oxidative carbonylation of the alcohol occurs, thereby obtaining a carbonic acid diester, wherein a heat of reaction is removed by the latent heat of vaporization of the alcohol used as a raw material.

In a particular mode of the process, at least part of the alcohol as a raw material is fed in liquid phase into a fluidized bed of the reactor.

In another mode of the process, cooling pipes are provided in a fluidized bed of the reactor and at least part of the alcohol as a raw material is introduced in liquid phase into the cooling pipes as a heat transfer medium so that at least part of the liquid alcohol is vaporized and fed into the fluidized-bed reactor. In this mode of the process, carbon monoxide can be introduced together with the liquid alcohol into the cooling pipes.

In the above modes of the process, cooling pipes in which water or an oil is introduced as a heat transfer medium can be provided in a fluidized bed of the reactor.

In the present invention, the process can be conducted in such a mode that cooling pipes are provided in a fluidized bed of the reactor and the alcohol as a raw material is introduced in liquid phase thereinto as a heat transfer medium so that the liquid alcohol is heated to an increased temperature, the heated liquid alcohol is fed into an evaporator in which the liquid alcohol is mixed with carbon monoxide and at least part of the alcohol is vaporized, and the vaporized alcohol is fed together with the carbon monoxide into the fluidized-bed reactor.

In the present invention, moreover, the process can be conducted in such a mode that cooling pipes are provided in a fluidized bed of the reactor and water or an oil as a heat transfer medium is circulated therethrough, the obtained hot water or hot oil being passed through a heat exchanger to thereby effect a heat exchange between the hot water or oil and a liquid alcohol so that the liquid alcohol is heated to have an increased temperature, the heated liquid alcohol is fed into an evaporator in which the liquid alcohol is mixed with carbon monoxide and at least part of the alcohol is vaporized, and the vaporized alcohol is fed together with the carbon monoxide into the fluidized-bed reactor.

The apparatus for producing a carbonic acid diester according to the present invention comprises:

a fluidized-bed reactor 1 adapted to carry out a reaction in a vapor phase of an alcohol, carbon monoxide and oxygen in the presence of a catalyst so that an oxidative carbonylation of the alcohol occurs to thereby form a carbonic acid diester, an evaporator 12 adapted to mix a liquid alcohol with carbon monoxide and vaporize at least part of the alcohol to thereby form a gaseous mixture of alcohol and carbon monoxide and adapted to feed the gaseous mixture through a gas supply line 3 into the fluidized-bed reactor 1, cooling pipes 7 arranged in the fluidized-bed reactor 1 and adapted to cause a liquid alcohol 9 as a heat transfer medium 8 capable of removing a heat of reaction generated by the oxidative carbonylation of the alcohol in the fluidized-bed reactor 1 to flow therethrough, and a heated alcohol supply line 14 adapted to feed the liquid alcohol 9 heated in the fluidized-bed reactor 1 from the cooling pipes 7 into the evaporator 12.

Furthermore, the apparatus for producing a carbonic acid diester according to the present invention may comprise:

the fluidized-bed reactor 1, the evaporator 12, cooling pipes 7 arranged in the fluidized-bed reactor 1 and adapted to cause a heat transfer medium 8 capable of removing a heat of reaction generated by the oxidative carbonylation of the alcohol in the fluidized-bed reactor 1 to flow therethrough, a heat transfer medium withdrawal line 17 adapted to lead the heat transfer medium 8 heated in the fluidized-bed reactor 1 from the cooling pipes 7 to a heat exchanger 19, the heat exchanger 19 adapted to conduct a heat exchange between the heat transfer medium 8 and a liquid alcohol 9 so that the liquid alcohol 9 is heated to an increased temperature, and a heated alcohol supply line 12g adapted to feed the liquid alcohol 9 heated by the heat exchanger 19 into the evaporator 12.

DETAILED DESCRIPTION OF THE INVENTION

The process for producing a carbonic acid diester and the apparatus for producing a carbonic acid diester according to the present invention will be described in detail below.

Process for producing carbonic acid diester

The present invention provides a process for producing a carbonic acid diester, which comprises carrying out a reaction in a vapor phase of an alcohol, carbon monoxide and oxygen in the presence of a catalyst in a fluidized-bed reactor so that an oxidative carbonylation of the alcohol occurs, thereby obtaining a carbonic acid diester, wherein a heat of reaction is removed by the latent heat of vaporization of the alcohol used as a raw material. In particular, at least part of a liquid alcohol as a raw material of the carbonylation is vaporized by the heat of reaction and, simultaneously, the heat of reaction is removed by the latent heat of vaporization of the alcohol, and the vaporized alcohol is subjected to the carbonylation.

For example, in one mode of the process, at least part of an alcohol as a raw material of the carbonylation is directly fed in liquid phase into the fluidized bed.

Figure 1:
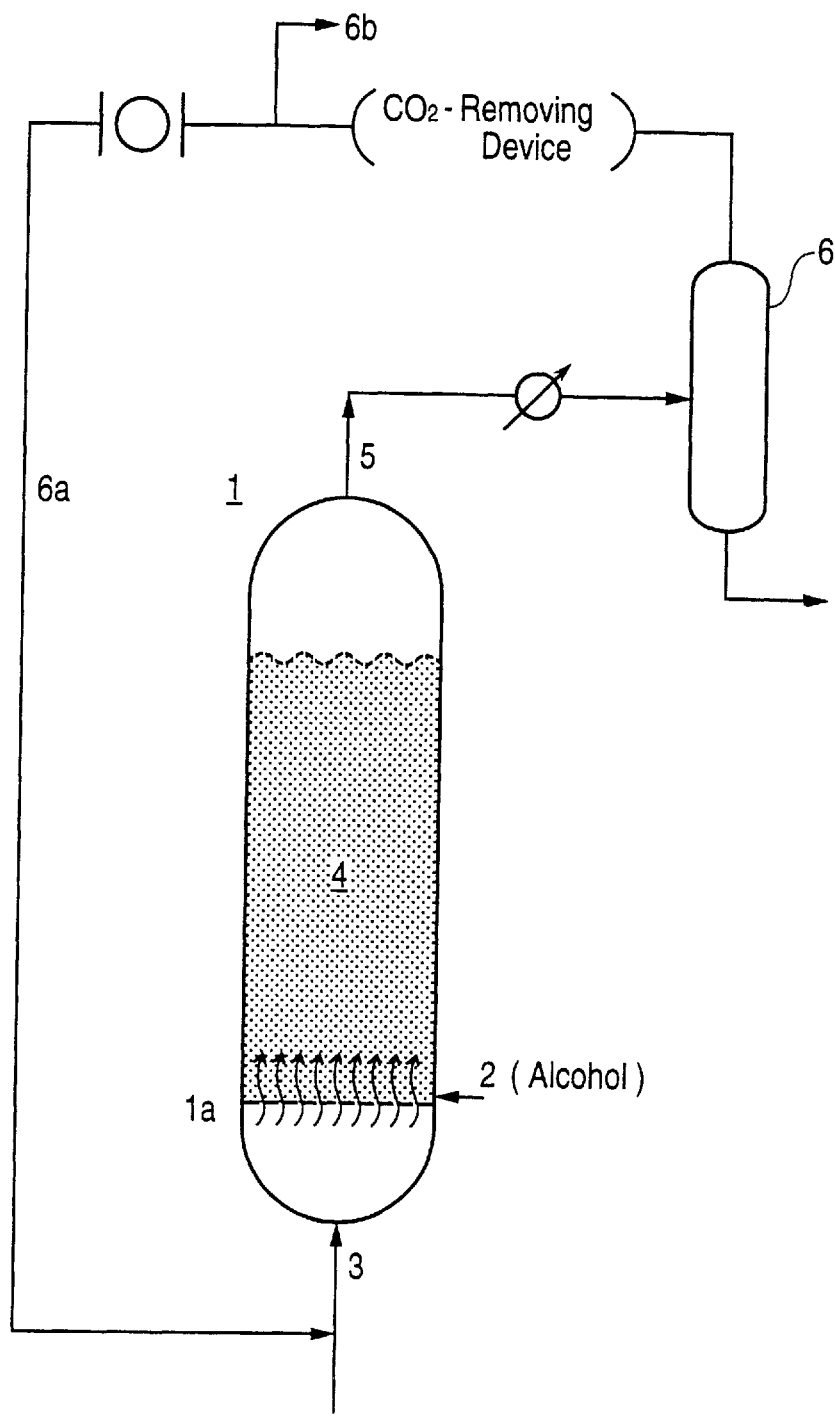
FIG. 1 schematically shows one mode of the process for producing a carbonic acid diester according to the present invention.

This process is schematically shown in FIG. 1.

Referring to FIG. 1, a fluidizing gas is introduced into a fluidized-bed reactor 1 charged with a solid catalyst through a gas supply line 3 provided at a bottom of the fluidized-bed reactor 1 and is fed through a gas distributor 1a provided in the reactor 1 so that the solid catalyst forms a fluidized bed 4. An inert gas such as nitrogen can also be used as an initial fluidizing gas to form the fluidized bed. The carbonylation is initiated by replacing the inert gas with a gas of a raw material.

Carbon monoxide and oxygen are generally introduced through the gas supply line 3 and fed through the gas distributor 1a into the fluidized bed 4 in order to perform the carbonylation in the vapor phase in the presence of a catalyst. At least part of the alcohol as a raw material is directly introduced in liquid phase into the fluidized bed 4 through, for example, a line 2.

Upon the feeding of the alcohol in liquid phase into the fluidized bed 4, the alcohol is vaporized to thereby undergo the carbonylation in the vapor phase and, simultaneously, the heat of reaction is removed by the latent heat of vaporization of the alcohol.

Simultaneously with the above liquid alcohol, vaporized alcohol can be introduced into the fluidized bed 4 by feeding the alcohol vaporized in advance through, for example, a line 3.

At least part of the alcohol may be introduced in liquid phase in the above direct feeding of the liquid alcohol into the fluidized bed 4. Although the proportion of the alcohol fed in liquid phase varies depending on the reaction conditions and the relationship in magnitude between the heat of reaction and the latent heat of vaporization, this proportion can be calculated on the basis of the quantity which can be vaporized by the heat of reaction and generally ranges from about 20 to 100%, preferably, from about 70 to 100% based on the total amount of the alcohol used in the carbonylation.

The feeding of the liquid alcohol is generally conducted at a pressure which is higher than the reaction pressure so that the liquid alcohol can be fed into the fluidized bed and at a temperature at which the alcohol can maintain its liquid state at the feeding pressure.

The reaction product is generally withdrawn through a line 5 provided at the top of the fluidized-bed reactor.

The oxygen introduced through the line 3 for the carbonylation may be pure molecular oxygen or may be one diluted with an inert gas such as nitrogen or argon.

The carbon monoxide introduced for the carbonylation is not limited to pure carbon monoxide. A gas which contains carbon monoxide may be used. Examples of such gases include a gaseous mixture of carbon monoxide and other components which are inert in the reaction, such as nitrogen, methane, hydrogen or carbon dioxide.

Although the carbon monoxide concentration of such a gaseous mixture is not particularly limited, it is generally preferred to be at least 70% from the economic point of view in the production of the carbonic acid diester.

The product gas from the fluidized-bed reactor can be recycled as a carbon monoxide source.

In the execution of the recycling, for example, part of the product gas from the fluidized-bed reactor 1 can be cooled and introduced into a vapor-liquid separator 6 by which the gas is separated from the liquid, and the separated gas can be compressed and recycled through a gas recycle line 6a to the fluidized-bed reactor 1, as shown in FIG. 1.

The gas separated by the vapor-liquid separator 6 may be introduced into a $CO_2$-removing device in which at least part of carbon dioxide formed as a by-product is removed by absorption or adsorption before the circulation to the fluidized-bed reactor 1. Further, part of the recycle gas may be discharged from a branch pipe 6b so that the concentration of impurities such as carbon dioxide is controlled.

Carbon monoxide may be added to the recycle gas at an arbitrary point (not shown) of the recycle line 6a.

Herein, as apparent from the above, the "carbon monoxide source" is used to mean not only pure carbon monoxide but also a gaseous mixture and a product gas which contain carbon monoxide collectively.

On the other hand, the liquid phase separated by the vapor-liquid separator 6 is generally led to a purification step (not shown), in which the liquid is, for example, distilled to obtain the desired carbonic acid diester.

Figure 2:
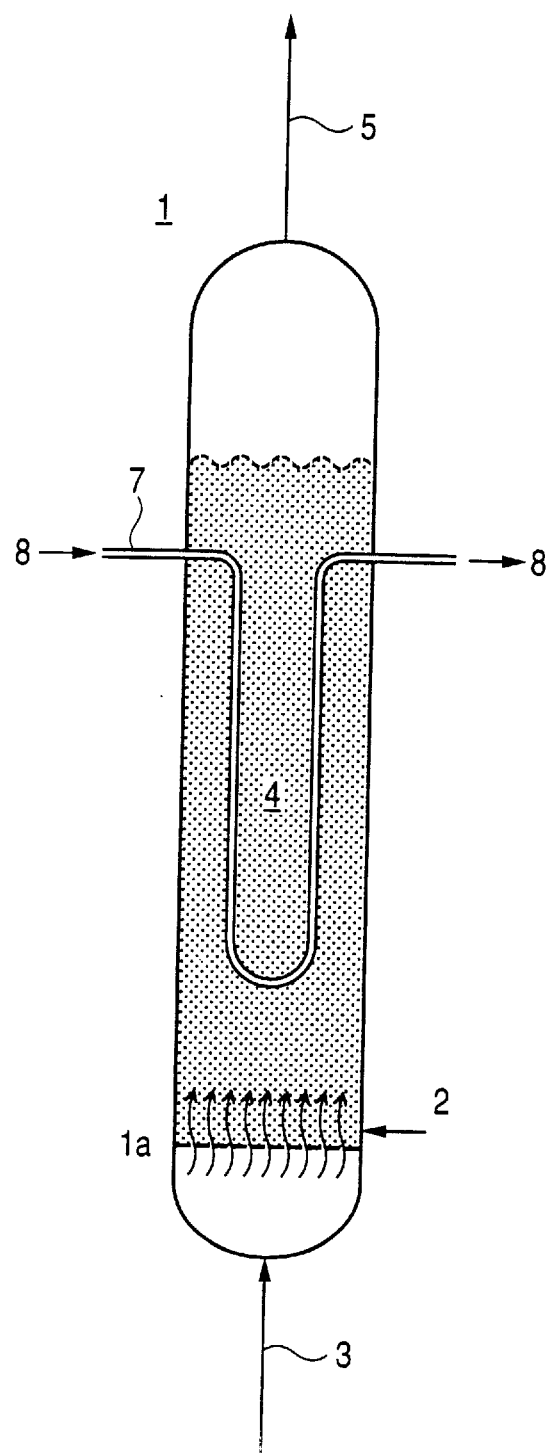
FIG. 2 shows another mode of the process for producing a carbonic acid diester according to the present invention.

In the present invention, the removal of the heat of reaction from the fluidized bed may be accomplished only by the above latent heat of vaporization of the alcohol. In addition to the latent heat of vaporization of the alcohol, the removal of the heat of reaction may be performed with the aid of cooling pipes 7 inserted in the fluidized bed 4 as shown in FIG. 2. Water or an oil can be used as a heat transfer medium 8 for the cooling pipes 7. For example, water heated at 70° to 100° C. may be used as the heat transfer medium.

Examples of suitable oils include commercially available heat transfer fluids comprising as a principal component an aromatic hydrocarbon such as diphenyl or terphenyl or an aromatic ether such as diphenyl ether and silicone oils.

A required number of cooling pipes 7 are provided in the fluidized bed. Reference characters in FIG. 2 correspond to those in FIG. 1.

Figure 3:
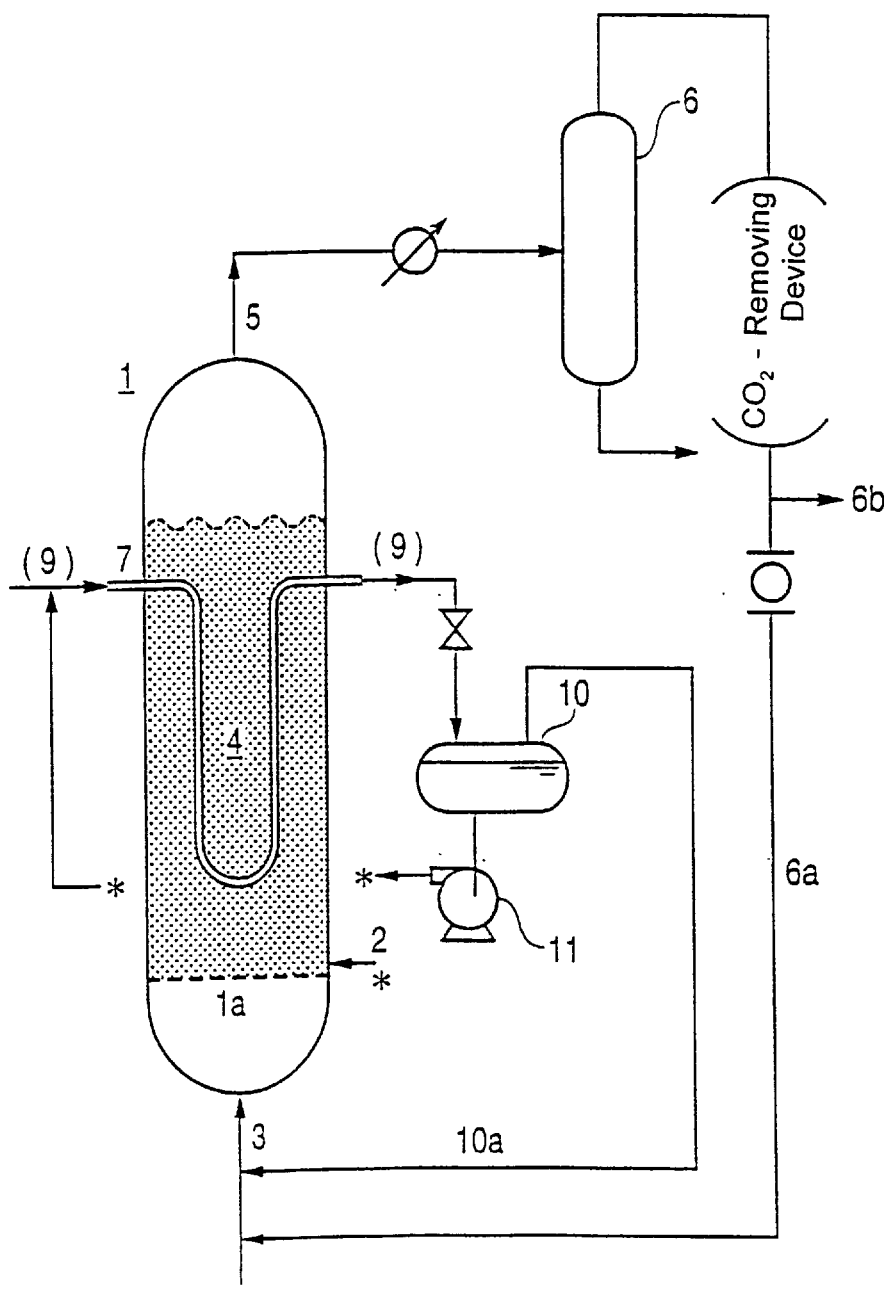
FIG. 3 shows a further other mode of the process for producing a carbonic acid diester according to the present invention.

In the present invention, the heat of reaction can be removed by the latent heat of vaporization of the alcohol as a raw material of the carbonylation in another mode of the process as shown in FIG. 3. Reference characters in FIG. 3 correspond to those in FIG. 1.

Referring now to FIG. 3, at least part of an alcohol as a raw material of the carbonylation is introduced in liquid phase as a heat transfer medium 9 in cooling pipes 7 arranged in a fluidized bed 4 and at least part of the liquid alcohol is vaporized and fed into the fluidized-bed reactor 1. The liquid alcohol introduced in the cooling pipes 7 is heated in the fluidized-bed 4, so that at least part thereof is vaporized and, simultaneously, the heat of reaction can be removed.

The above use of the alcohol as the heat transfer medium 9 passed through the cooling pipes 7 enables the alcohol to be heated to substantially the same temperature as the reaction temperature. Therefore, even if the reaction temperature is as low as about 130° to 170° C., at least part, preferably, all of the alcohol heated to the reaction temperature can be obtained in vapor phase, so that the heat of reaction can effectively be utilized.

The alcohol 9 vaporized in the cooling pipes 7 is introduced in an optionally installed vapor-liquid separator 10 by which liquid alcohol is separated. The vaporized alcohol after the separation is recycled through, for example, a line 10a and a line 3 to the fluidized-bed reactor 1. After the separation by the vapor-liquid separator 10, the liquid alcohol may be, for example, recycled as the heat transfer medium 9 to the cooling pipes 7 by means of a pump 11 or can directly be introduced in the fluidized bed 4 through the line 2 as shown in FIG. 1.

In the present invention, in the above mode of the process shown in FIG. 3, a carbon monoxide source together with the liquid alcohol can be introduced in the cooling pipes 7 as the heat transfer medium 9. Use of mixture of the alcohol and carbon monoxide decreases the boiling point of the alcohol and makes it easy not only to vaporize the alcohol but also to remove the heat of reaction because of the increase of the difference between the reaction temperature and the boiling point of the alcohol.

The carbon monoxide source introduced together with the liquid alcohol in the cooling pipes 7 is not limited to pure carbon monoxide. A gaseous mixture of carbon monoxide, a gas which is inert in the reaction or a product gas withdrawn from the fluidized-bed reactor as mentioned above can be used as the carbon monoxide source.

The resultant mixture of the alcohol heated in the cooling pipes 7, and thus at least partially vaporized, and carbon monoxide can be introduced in the above optionally installed vapor-liquid separator 10 by which liquid alcohol is removed and fed through the line 10a and the line 3 into the fluidized bed 4.

For removing the heat of reaction by the above process, it is satisfactory that at least part of the alcohol for use in the carbonylation is introduced in liquid phase in the cooling pipes 7 as the heat transfer medium 9. The proportion of the alcohol fed in the cooling pipes 7 generally ranges from about 20 to 100%, preferably, from about 70 to 100% based on the total amount of the alcohol used in the carbonylation.

In the introduction of the alcohol-containing gas produced by the vaporization in the cooling pipes 7 in the fluidized-bed reactor 1, the operation must be conducted under such conditions that the pressure of the alcohol-containing gas at the temperature of the outlet of the cooling pipes 7 is higher than the reaction pressure so as to enable of the above introduction.

Figure 4:
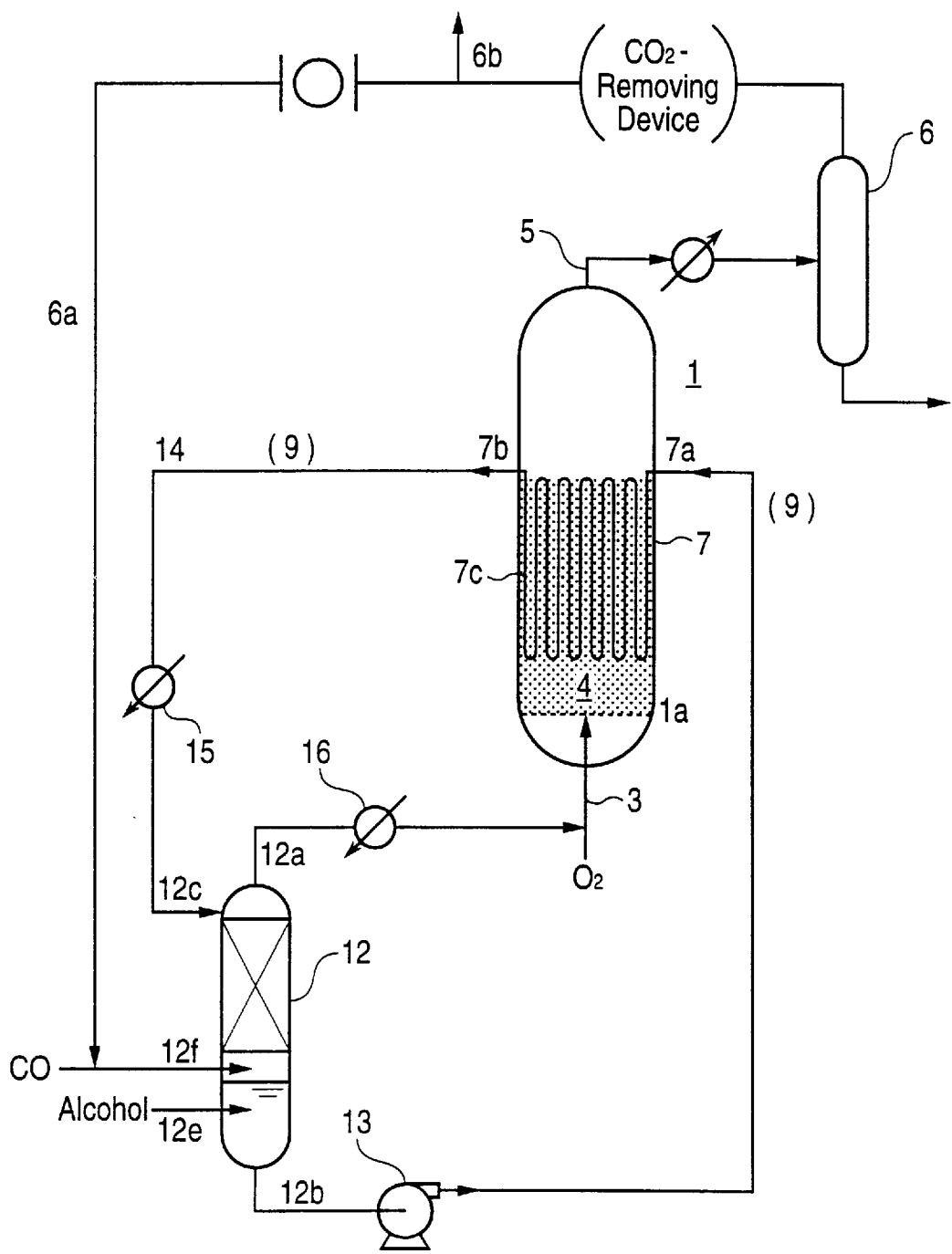
FIG. 4 shows one form of the apparatus for producing a carbonic acid diester according to the present invention.

In the present invention, still further, the carbonic acid diester can be produced while vaporizing the alcohol by the heat of reaction according to the mode of the process as shown in FIG. 4. That is, cooling pipes 7 are provided in a fluidized bed 4 of a reactor and an alcohol as a raw material is introduced in liquid phase thereinto as a heat transfer medium 9 so that the liquid alcohol is heated to have an increased temperature. Subsequently, the heated liquid alcohol is fed into an evaporator 12 in which the liquid alcohol is mixed with carbon monoxide and at least part of the alcohol is vaporized. The vaporized alcohol can be fed together with the carbon monoxide into the fluidized-bed reactor. Reference characters in FIG. 4 correspond to those in FIGS. 1 to 3.

Referring to FIG. 4, the evaporator 12 may be provided with an alcohol supply line 12e and the above alcohol as the heat transfer medium 9 may be fed from the bottom of the evaporator 12 through a recycle line 12b into the cooling pipes 7 by means of a pump 13. The alcohol supply line 12e may be provided at any arbitrary point (not shown) of the recycle line 12b extending from the bottom of the evaporator to the reactor inlet side 7a of the cooling pipes 7.

An alcohol supply line may directly be provided on the reactor inlet side 7a of the cooling pipes 7 without providing the recycle line 12b extending from the bottom of the evaporator to the cooling pipes 7.

The alcohol 9 passing through the cooling pipes 7 removes the heat of reaction from the fluidized bed 4 and, simultaneously, is heated to an increased temperature. The heated alcohol 9 is introduced through an alcohol supply line 14 from a top part 12c of the evaporator into the evaporator 12.

The heated liquid alcohol is mixed with carbon monoxide (the mole fraction of the alcohol lowered) in the evaporator 12, so that the boiling point of the alcohol is lowered to thereby cause at least part of the alcohol to vaporize.

Although the type of the evaporator 12 is not limited as long as the vapor and the liquid can satisfactorily contact each other, a packed column and a plate column are preferred. A packed column is especially preferred from the viewpoint that the pressure drop is low.

The pressure of the evaporator 12 is preferred to be at least 0.1 kg/cm$^2$, especially, at least 0.5 kg/cm$^2$ higher than the reaction pressure. From the economic point of view, it is preferred that the difference between the pressure of the evaporator 12 and the reaction pressure is not greater than about 1 kg/cm$^2$.

In the evaporator 12, it is preferred that the alcohol is mixed with carbon monoxide so that a gaseous mixture of carbon monoxide and alcohol with a molar ratio (CO/alcohol) subjected to the below described reaction system can be obtained.

Therefore, the temperature of an evaporator outlet 12a is set on the basis of the calculation from the pressure of the evaporator and the alcohol concentration of the gaseous mixture.

For example, in the synthesis of dimethyl carbonate, when the pressure of the top of the evaporator 12 is 9.2 atm and the alcohol concentration of the evaporator is 22 mol%, the temperature of the evaporator outlet 12a is set at 85° C. which is the dew point of the gaseous mixture.

The temperature of the liquid alcohol as the heat transfer medium 9 at a reactor outlet side 7b of the cooling pipes is preferred to have a temperature which is higher than, especially, at least 3° C. higher than the temperature of the evaporator outlet 12a.

For example, when the temperature of the evaporator outlet 12a is set at 85° C. as mentioned above, the temperature of the alcohol at the reactor outlet side 7b is preferred to be at least 88° C.

The thus obtained gaseous mixture of vaporized alcohol and carbon monoxide is discharged from the evaporator outlet 12a and fed through a gas supply line 3 into the fluidized-bed reactor 1. This gaseous mixture may be heated by a heat exchanger 16 as necessary before being fed through the gas supply line 3 into the fluidized-bed reactor 1.

The alcohol can be supplied in an amount corresponding to the amount of alcohol consumed by the carbonylation through the line 12e into the evaporator 12 while controlling the level of the alcohol. On the other hand, carbon monoxide can be supplied through a line 12f into the evaporator 12. Oxygen can be supplied through the line 3.

In the above modes of the process shown in FIGS. 3 and 4, when the quantity of the heat of reaction is larger than the quantity of heat required for the vaporization of the alcohol, the heat removal can be effected by providing in the fluidized bed 4 a suitable number of other cooling pipes 7 through which, for example, water flows as the heat transfer medium 8 as necessary in addition to the above cooling pipes 7 through which the alcohol flows as the heat transfer medium 9.

In the mode of the process shown in FIG. 4, when the quantity of the heat of reaction is larger than the quantity of heat required for the vaporization of the alcohol, alternatively, the heated alcohol supply line 14 can be provided with an auxiliary heat exchanger 15 so that the alcohol is cooled to an appropriate temperature by, for example, a cooling water before being fed into the evaporator 12.

When the quantity of the heat of reaction is smaller than the quantity of heat required for the vaporization of the alcohol, the auxiliary heat exchanger 15 can be used as a heater. In the use as a heater, steam or electric power can be employed as the heat source.

Figure 5:
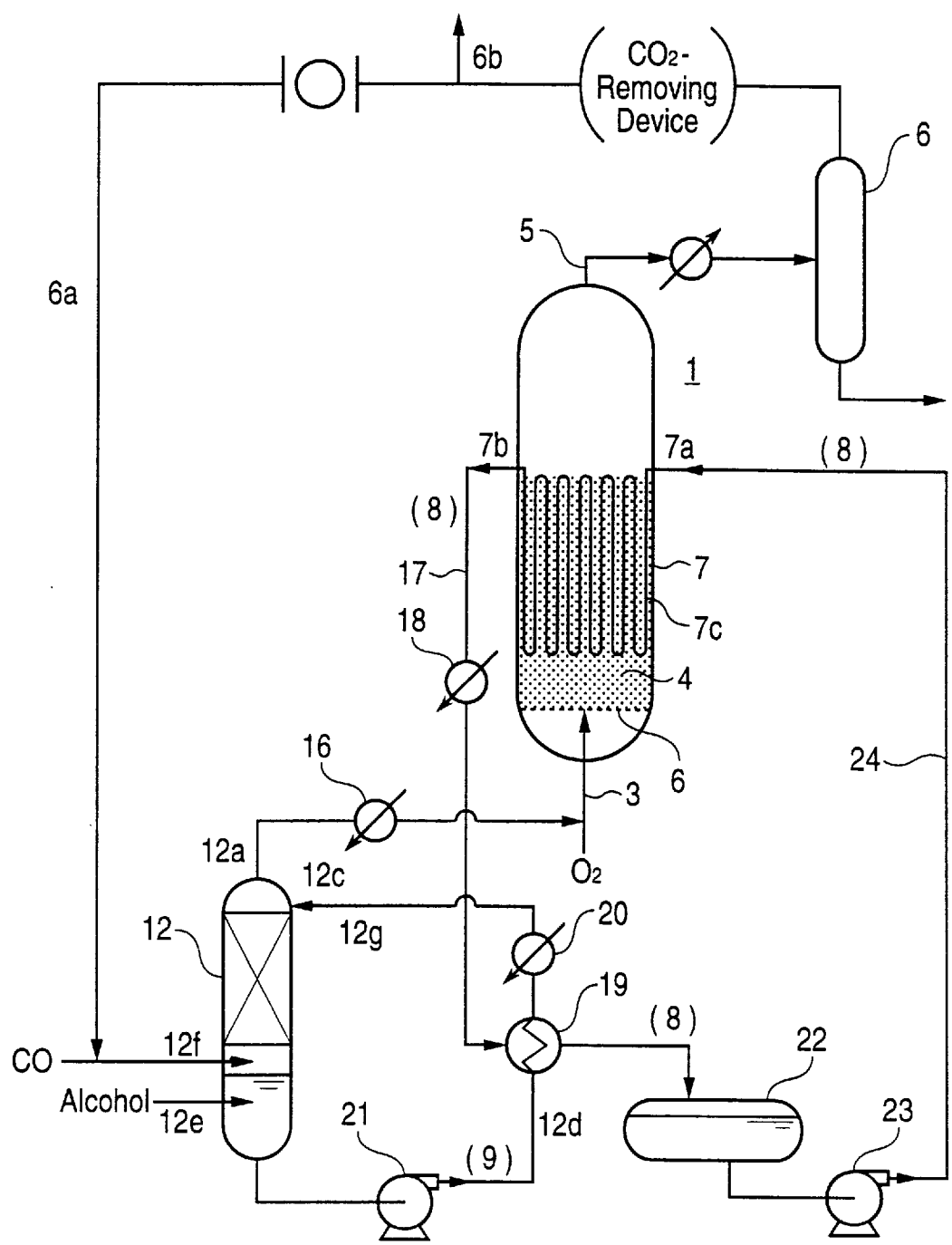
FIG. 5 shows another form of the apparatus for producing a carbonic acid diester according to the present invention.

In the present invention, still further, the carbonic acid diester can be produced while vaporizing the alcohol by the heat of reaction according to the mode of the process as shown in FIG. 5. Reference characters in FIG. 5 correspond to those in FIG. 4. This mode of the process can be carried out in the following manner.

Cooling pipes 7 are provided as in the above mode and water or an oil as a heat transfer medium 8 is circulated therethrough to thereby obtain hot water or hot oil, this hot water or hot oil 8 being passed through a heat exchanger 19 to thereby effect a heat exchange between the hot water or oil and a liquid alcohol so that the liquid alcohol is heated to an increased temperature. This heated liquid alcohol is fed into an evaporator 12 in which the liquid alcohol is mixed with carbon monoxide and at least part of the alcohol is vaporized as in the above mode of the process shown in FIG. 4. The vaporized alcohol is fed together with the carbon monoxide into the fluidized-bed reactor 1.

The heat transfer medium (water or an oil) 8 which flows through the cooling pipes 7 arranged in the fluidized bed 4 removes the heat of reaction and, simultaneously, is heated. The resultant hot water or hot oil is discharged from the reactor outlet side 7b and led through a heat transfer medium withdrawal line 17 into the heat exchanger 19 in which the hot water or hot oil undergoes a heat exchange with the alcohol.

The heat transfer medium 8 cooled by the heat exchanger 19 is recycled to the fluidized-bed reactor 1 as necessary. When the heat transfer medium 8 is recycled, the heat transfer medium 8 cooled by the heat exchanger 19 can first be stored in a heat transfer medium drum 22 and, then, recycled through a line 24 by means of a pump 23 to be introduced in the cooling pipes 7.

The alcohol as a raw material of the carbonylation is heated to an increased temperature by the heat transfer medium 8 in the heat exchanger 19 and, then, fed through a line 12g to a top part 12c of the evaporator.

In the evaporator 12, as in the mode of the process shown in FIG. 4, the heated liquid alcohol is mixed with carbon monoxide and thereby vaporized. The thus produced gaseous mixture of alcohol and carbon monoxide is discharged from an evaporator outlet 12a and fed through a gas supply line 3 into the fluidized-bed reactor 1.

This gaseous mixture can be heated by means of a heat exchanger 16 as necessary before being fed through the gas supply line 3 into the fluidized-bed reactor 1.

In the above mode of the process, the alcohol 9 is generally discharged from the bottom of the evaporator 12 and fed through a line 12d into the heat exchanger 19 by means of a pump 21 so that the alcohol 9 is heated to an increased temperature by the heat exchange with the heat transfer medium 8. The heated alcohol is fed through the line 12g into the evaporator 12.

In the evaporator 12, it is preferred that the alcohol is mixed with carbon monoxide so that a gaseous mixture of carbon monoxide and alcohol with a molar ratio which is suitable for the below described reaction system can be obtained.

Therefore, the temperature of the evaporator outlet 12a is set on the basis of the calculation from the pressure of the evaporator and the desired alcohol concentration of the gaseous mixture.

For example, in the synthesis of dimethyl carbonate, when the pressure of the top of the evaporator 12 is 9.2 atm and the alcohol concentration of the gaseous mixture is 22 mol%, the temperature of the evaporator outlet 12a is set at 85° C. which is the dew point of the gaseous mixture.

Thus, it is requisite that the temperature of the methanol fed through the line 12g to the top part 12c of the evaporator is higher than the temperature of the evaporator outlet 12a (85° C.) and that the temperature of the heat transfer medium at the reactor outlet side 7b is still higher than the temperature of the methanol fed to the evaporator. For effective heat exchange, it is desired that the temperature of the methanol at the top part 12c of the evaporator is at least 3° C. higher than the temperature of the gas of the line 12a and that the temperature of the heat transfer medium at the reactor outlet side 7b is at least 3° C. higher than the temperature of the methanol at the top part 12c of the evaporator.

The alcohol can be supplied in an amount corresponding to the amount of alcohol consumed by the carbonylation through the line 12e into the evaporator 12 while controlling the level of the alcohol. On the other hand, carbon monoxide can be supplied through a line 12f into the evaporator 12. Oxygen can be supplied through the line 3. The position of the alcohol supply line 12e does not necessarily have to be the bottom of the evaporator and can be at any arbitrary point of the line 12d extending to the heat exchanger 19. Further, an alcohol supply line may be directly provided on the heat exchanger 19 without providing the recycle line 12d extending from the bottom of the evaporator to the heat exchanger 19.

When the quantity of the heat of reaction is larger than the quantity of heat required for the vaporization of the alcohol, it is appropriate to discharge part of the cooling medium outside the system without recycling it or to provide the heat transfer medium withdrawal line 17 with an auxiliary heat exchanger 18 so that the alcohol is cooled. On the other hand, when the quantity of the heat of reaction is smaller than the quantity of heat required for the vaporization of the alcohol, it is appropriate to install the auxiliary heat exchanger 18 or a heat exchanger 20 so that the alcohol is heated.

In the present invention, as described above, the alcohol, carbon monoxide and oxygen react in the vapor phase in the presence of a catalyst while removing the heat of reaction with the direct or indirect utilization of the latent heat of vaporization of the alcohol as a raw material of the carbonylation, thereby obtaining the carbonic acid diester.

The above alcohol is, for example, an aliphatic alcohol having 1 to 6 carbon atoms, an alicyclic alcohol or an aromatic hydroxyl compound.

Examples of suitable alcohols are monohydric alcohols including saturated aliphatic alcohols such as methanol, ethanol, propanol, butanol, pentanol and hexanol, unsaturated aliphatic alcohols such as allyl alcohol, alicyclic alcohols such as cyclopropanol, cyclobutanol, cyclopentanol and cyclohexanol, and aromatic hydroxyl compounds such as phenol and benzyl alcohol.

These are used either individually or in combination. Of these, methanol and ethanol are preferred.

In the above reaction system, carbon monoxide is generally used in a molar ratio to alcohol (CO/alcohol) of 0.2 to 100, preferably, 0.5 to 20 and, still preferably, 1 to 10. Oxygen is generally used in a molar ratio to alcohol ($O_2$/alcohol) of 0.01 to 0.5, preferably, 0.05 to 0.3 and, still preferably, 0.05 to 0.2.

In the reaction of the above alcohol, carbon monoxide and oxygen, the reaction temperature is generally preferred to range from 70° to 350° C., especially, from 8° to 250° C., still especially, from 100° to 200° C. and, yet still especially, from 130° to 170° C. The reaction pressure is generally preferred to range from atmospheric pressure to 35 kg/cm²G, especially, from 2 to 20 kg/cm²G.

In the present invention, use can be made of a wide variety of solid catalysts which are commonly employed as catalysts for the oxidative carbonylation of alcohol. Examples of such solid catalysts for the oxidative carbonylation include those comprising a support such as active carbon and, carried thereon, a catalytic component such as a metal halide, a mixed metal halide or a metal oxyhalide.

Of suitable metal halides, preferred use is made of a monovalent or divalent copper halide such as copper chloride or copper bromide. Specific examples of suitable solid catalysts include catalysts having, carried on a support, not only a copper halide, but also (1) an alkali metal hydroxide and/or an alkaline earth metal hydroxide, e.g., lithium hydroxide, sodium hydroxide, potassium hydroxide, barium hydroxide and/or calcium hydroxide, (2) Japanese Patent Publication No. 7(1995)-10352, catalysts having, carried on a support, not only a copper halide but also a tertiary organophosphorus compound having a phenyl or an alkyl group such as triphenylphosphine, an alkylarylphosphine, a trialkyl phosphite or a trialkyl phosphate, (3) the International Application Publication WO 90/15791 and catalysts having, carried on a support, not only a copper halide but also an inorganic carbonate such as $K_2CO_3$, $Na_2CO_3$, $CaCO_3$, $BaCO_3$, $KNaCO_3$, $KHCO_3$ or $(NH_4)_2CO_3$, (4) Japanese Patent Laid-open Publication No. 7(1995)-194983.

The above catalysts can be prepared according to the usual methods such as impregnation, milling and coprecipitation methods commonly employed in causing a catalytic component to be carried on a support.

Examples of the carbonic acid diesters produced by the above modes of the process according to the present invention include dimethyl carbonate, diethyl carbonate, dipropyl carbonate, dibutyl carbonate, dipentyl carbonate, dihexyl carbonate, dicyclopropyl carbonate, dicyclobutyl carbonate, dicyclopentyl carbonate, dicyclohexyl carbonate, dibenzyl carbonate, methyl ethyl carbonate, methyl propyl carbonate and ethyl propyl carbonate.

Apparatus for producing carbonic acid diester

The present invention provides an apparatus which is suitable for the production of a carbonic acid diester according to the above modes of the process shown in FIGS. 4 and 5.

One form of the apparatus for producing a carbonic acid diester according to the present invention is shown in FIG. 4.

One form of the apparatus for producing a carbonic acid diester according to the present invention comprises:

a fluidized-bed reactor 1 adapted to carry-out a reaction in a vapor phase of an alcohol, carbon monoxide and oxygen in the presence of a catalyst so that an oxidative carbonylation of the alcohol occurs to thereby form a carbonic acid diester, an evaporator 12 adapted to mix a liquid alcohol with carbon monoxide and vaporize at least part of the alcohol to thereby form a gaseous mixture of alcohol and carbon monoxide and adapted to feed the gaseous mixture through a gas supply line 3 into the fluidized-bed reactor 1, cooling pipes 7 arranged in the fluidized-bed reactor 1 and adapted to cause the formation of a liquid alcohol 9 as a heat transfer medium capable of removing a heat of reaction generated by the oxidative carbonylation of the alcohol in the fluidized-bed reactor 1 to flow therethrough, and a heated alcohol supply line 14 adapted to feed the liquid alcohol 9 heated in the fluidized-bed reactor 1 from the heat cooling pipes 7 into the evaporator 12.

The above fluidized-bed reactor 1 is provided at a lower part thereof with a gas distributor 1a and provided at the top thereof with a product withdrawal line 5.

Although the type of the evaporator 12 is not particularly limited as long as it is capable of mixing the liquid alcohol with carbon monoxide and thus is capable of effecting vaporization of the liquid alcohol, for example, the evaporator can be of the type designed to bring the liquid alcohol and carbon monoxide into a counterflow contact.

The evaporator 12 is provided with an alcohol supply line 12e and a carbon monoxide supply line 12f. If necessary, a heat exchanger 16 may be interposed between an evaporator outlet 12a of the evaporator and the supply line 3.

A line 12b is generally arranged extending from the bottom of the evaporator 12 to the reactor inlet side 7a of the cooling pipes 7 and is provided with a pump 13 in the middle thereof, so that the alcohol can be fed to the cooling pipes 7.

The alcohol supply line 12e may be disposed at any arbitrary position of the line 12b.

The heated alcohol supply line 14 may be provided with a heat exchanger 15.

Moreover, this apparatus may be provided with a vapor-liquid separator 6 by which the product gas withdrawn through the line 5 from the fluidized-bed reactor 1 is separated into a gas and a liquid and further provided with a gas recycle line 6a adapted to recycle the gas separated by the vapor-liquid separator 6 to the evaporator 12. This gas recycle line 6a may be provided with a $CO_2$-removing device capable of removing by-product carbon dioxide from the gas separated by the vapor-liquid separator 6 by absorption or adsorption.

This gas recycle line 6a may be provided with a branch pipe 6b capable of discharging the gas outside the reaction system.

Another form of the apparatus for producing a carbonic acid diester according to the present invention is shown in FIG. 5. Reference characters in FIG. 5 correspond to those in FIG. 4.

This form of apparatus for producing a carbonic acid diester according to the present invention may comprise:

the fluidized-bed reactor 1, the evaporator 12, cooling pipes 7 arranged in the fluidized-bed reactor 1 and adapted to form a heat transfer medium 8 capable of removing a heat of reaction generated by the oxidative carbonylation of the alcohol in the fluidized-bed reactor 1 to flow therethrough, a heat transfer medium withdrawal line 17 adapted to lead the heat transfer medium 8 heated in the fluidized-bed reactor 1 from the cooling pipes 7 to a heat exchanger 19, the heat exchanger 19 adapted to conduct a heat exchange between the heat transfer medium 8 and liquid alcohol 9 so that the liquid alcohol 9 is heated to an increased temperature, and a heated alcohol supply line 12g adapted to feed the liquid alcohol 9 heated by the heat exchanger 19 into the evaporator 12.

In this form of the apparatus, it is generally preferred that water or an oil is used as the heat transfer medium 8.

The heat transfer medium withdrawal line 17 may be provided with an auxiliary heat exchanger 18. Further, the apparatus may be provided with a line 24 through which the heat transfer medium 8 cooled by the heat exchange with the alcohol by means of the heat exchanger 19 is recycled to the cooling pipes 7 by means of a pump 23. This line 24 may be provided with a heat transfer medium drum 22 in which the heat transfer medium 8 having undergone the heat exchange is temporarily stocked.

The heated alcohol supply line 12g may be provided with an auxiliary heat exchanger 20. A line 12d extending from the bottom of the evaporator to the heat exchanger 19 is generally provided with a pump 21.

Moreover, this apparatus may be provided with a vapor-liquid separator 6 by which the product gas withdrawn through the line 5 from the fluidized-bed reactor 1 is separated into a gas and a liquid and further provided with a gas recycle line 6a adapted to recycle the gas separated by the vapor-liquid separator 6 to the evaporator 12. This gas recycle line 6a may be provided with a $CO_2$-removing device capable of removing by-product carbon dioxide from the gas separated by the vapor-liquid separator 6 by absorption or adsorption.

This gas recycle line 6a may be provided with a branch pipe 6b capable of discharging the gas outside the reaction system.

EFFECT OF THE INVENTION

The present invention provides a process for producing a carbonic acid diester in a vapor phase with the use of a fluidized-bed reactor, by which the carbonic acid diester can be produced in high energy efficiency by effective utilization of the heat of reaction.

Further, the present invention provides an apparatus for producing a carbonic acid diester which is suitable for use in carrying out the above process.

EXAMPLE

The present invention will now be illustrated in greater detail with reference to the following Examples, which in no way limit the scope of the invention.

In the following Examples and Comparative Examples, use was made of the catalyst prepared by causing active carbon to carry copper (II) chloride and sodium hydroxide in a molar ratio of OH/Cu of 1.2 and at a copper content of 6% by weight.

[Preparation of catalyst]

37 kg of copper (II) chloride dihydrate was dissolved in distilled water to obtain 100 lit. of an aqueous copper chloride solution (a).

13 kg of sodium hydroxide was dissolved in distilled water to obtain 100 lit. of an aqueous sodium hydroxide solution (b).

100 kg of active carbon was impregnated with 50 lit. of the above aqueous copper chloride solution (a), dried at 130° C. for 3 hr flowing nitrogen gas and cooled. The resultant copper chloride carrying active carbon was impregnated with 40 lit. of the above aqueous sodium hydroxide solution (b) and dried at 130° C. for 3 hr flowing nitrogen gas, thereby obtaining a catalyst for use in a fluidized bed.

This catalyst had a copper content of 6% by weight and a molar ratio of OH/Cu of 1.2. The Cu content was calculated by the formula:

$$\text{Cu content (wt. \%)} = \frac{\text{wt. of Cu}}{\text{wt. of } CuCl_2 + \text{wt. of active carbon}} \times 100$$

Example 1

Six U-shaped cooling pipes each having an outside diameter of 34 mm and a length of straight line part of 1 m were inserted in a fluidized-bed reactor of 350 mm in diameter having a height of catalyst-packed bed of 1500 mm. The U-shaped cooling pipes were arranged so as to allow respective cooling mediums different from each other to flow therethrough.

Nitrogen heated at 140° C. was fed at a flow rate of 112 kg/h into the fluidized-bed reactor through a gas distributor disposed at a bottom of the fluidized-bed reactor, and the pressure in the fluidized-bed reactor was controlled at 9 atm.

Subsequently, methanol which was heated to 140° C. and thereby vaporized was fed at a rate of 10 kg/h into the fluidized-bed reactor, and, further, CO and $O_2$ were fed with the feeding rate of nitrogen reduced so that the feeding rates of CO and $O_2$ were finally 112 kg/h and 9.6 kg/h, respectively, and the feeding of $N_2$ was discontinued.

Thereafter, a liquid methanol heated to 80° C. was directly fed just above the gas distributor into the fluidized bed at a rate of 5 kg/h. The feeding rate of the liquid methanol was gradually increased while the feeding rate of the vaporized methanol was gradually decreased until all the methanol became fed in liquid phase at a rate of 64 kg/h.

Under this condition, the reaction was continued for 6 hr. Throughout the reaction, cooling by passing 80° C. water through only three of the U-shaped cooling pipes enabled desirably controlling the reaction temperature at 140°±3° C.

The composition analysis and the flow rate measurement of the reactor effluent gas showed that the methanol conversion was 31% and the dimethyl carbonate (DMC) selectivity was 90%. The DMC yield determined from the material balance was 25 kg/h.

Comparative Example 1

The same fluidized-bed reactor as in Example 1 was used and the reaction pressure was controlled at 9 atm by nitrogen in the same manner as in Example 1.

Subsequently, methanol which was heated to 140° C. and thereby vaporized, CO and $O_2$ were fed into the fluidizedbed reactor at respective rates of 10, 112 and 9.6 kg/h, and the feeding of nitrogen was discontinued. 80° C. water was initially passed through only three of the cooling pipes, and, while gradually increasing the feeding rate of vaporized methanol, the number of cooling pipes through which hot water was passed was increased. However, when the feeding rate of vaporized methanol was increased to 50 kg/h, the reaction temperature continued to increase irrespective of the feeding of hot water to all of the six cooling pipes with the result that the $CO_2$ concentration of the effluent gas exhibited a grave increase.

Therefore, the feeding rate of vaporized methanol was decreased to 42 kg/h and the operation was continued for 6 hr. The reaction temperature could be controlled at 145°±5° C.

The methanol conversion, DMC selectivity and DMC yield were 29%, 89% and 15 kg/h, respectively.

It was found that the DMC yield of Example 1 was 1.7 times that of Comparative Example 1 and that the utility corresponding to 70% of the cooling duty and all the heat of vaporization of methanol could be saved in Example 1 as compared with those of Comparative Example 1.

Example 2

The same fluidized-bed reactor as in Example 1 was used and the reaction pressure was controlled at 4 atm by nitrogen in the same manner as in Example 1.

Subsequently, methanol which was heated to 140° C. and thereby vaporized was fed at a rate of 5 kg/h into the fluidized-bed reactor, and, further, CO and $O_2$ were fed with the feeding rate of nitrogen reduced so that the feeding rates of CO and $O_2$ were finally 52 kg/h and 4.5 kg/h, respectively, and the feeding of $N_2$ was discontinued.

Thereafter, a liquid methanol heated to 80° C. was directly fed just above the gas distributor into the fluidized bed at a rate of 5 kg/h. The feeding rate of the liquid methanol was gradually increased while the feeding rate of the vaporized methanol was gradually decreased until all the methanol became fed in liquid phase at a rate of 30 kg/h.

80° C. water was passed through only one of the U-shaped cooling pipes, and the reaction was continued for 5 hr.

The composition analysis and the flow rate measurement of the reactor effluent gas showed that the methanol conversion was 30% and the dimethyl carbonate (DMC) selectivity was 91%. The DMC yield determined from the material balance was 11 kg/h.

Example 3

The same fluidized-bed reactor as in Example 1 was used and the reaction pressure was controlled at 4 atm by nitrogen in the same manner as in Example 1.

Subsequently, methanol which was heated to 140° C. and thereby vaporized was fed at a rate of 5 kg/h into the fluidized-bed reactor, and, further, CO and $O_2$ were fed with the feeding rate of nitrogen reduced so that the feeding rates of CO and $O_2$ were finally 52 kg/h and 4.5 kg/h, respectively, and the feeding of $N_2$ was discontinued.

Thereafter, a liquid methanol was fed to four of the U-shaped cooling pipes, vaporized at pressure of 4.2 atm and fed into the fluidized bed reactor at a rate of 5 kg/h. Of the methanol fed into the fluidized-bed reactor, the feeding rate of the methanol vaporized in the cooling pipes was gradually increased while the feeding rate of the methanol vaporized outside the reactor was decreased until only the methanol vaporized in the cooling pipes became fed at a rate of 30 kg/h.

The reaction was continued for 5 hr under this condition while passing 80° C. water through another two of the cooling pipes.

The methanol conversion, DMC selectivity and DMC yield were 30%, 90% and 11 kg/h, respectively.

Example 4

The same fluidized-bed reactor as in Example 1 was used and the reaction pressure was controlled at 4 atm by nitrogen in the same manner as in Example 1.

Subsequently, methanol which was heated to 140° C. and thereby vaporized was fed at a rate of 5 kg/h into the fluidized-bed reactor, and, further, CO and $O_2$ were fed with the feeding rate of nitrogen reduced so that the feeding rates of CO and $O_2$ were finally 52 kg/h and 4.5 kg/h, respectively, and the feeding of $N_2$ was discontinued.

Thereafter, CO and a liquid methanol were mixed together and fed to three of the U-shaped cooling pipes, causing the methanol to vaporize at an intra-pipe temperature controlled at 95° C. and fed into the fluidized bed reactor. The feeding rates of the methanol and CO at the initial feeding points were decreased until the methanol and CO finally fed into the fluidized-bed reactor entirely through the cooling pipes. The vaporized methanol and CO were fed at respective rates of 30 kg/h and 52 kg/h.

The reaction was continued for 5 hr under this condition while passing 80° C. water through another two of the cooling pipes.

The methanol conversion, DMC selectivity and DMC yield were 30%, 91% and 11 kg/h, respectively.

Comparative Example 2

The same fluidized-bed reactor as in Example 1 was used and the reaction pressure was controlled at 4 atm by nitrogen in the same manner as in Example 1.

Subsequently, methanol which was heated to 140° C. and thereby vaporized, CO and $O_2$ were fed into the fluidized-bed reactor at respective rates of 10, 52 and 4.5 kg/h, and the feeding of nitrogen was discontinued. 80° C. water was initially passed through only one of the U-shaped cooling pipes, and, while gradually increasing the feeding rate of vaporized methanol, the number of cooling pipes through which hot water was passed was increased. Finally, the reaction temperature could be controlled at 145°±5° C. by increasing the feeding rate of vaporized methanol to 30 kg/h and by feeding hot water to five of the cooling pipes.

The methanol conversion, DMC selectivity and DMC yield were 28%, 89% and 10 kg/h, respectively.

It was found that the utility corresponding to 76% of the cooling duty and all the heat of vaporization of methanol could be saved in Examples 2 to 4 as compared with those of Comparative Example 2.

Example 5

The same fluidized-bed reactor as in Example 1 was used and the reaction pressure was controlled at 9 atm by nitrogen in the same manner as in Example 1.

Nitrogen heated to 140° C. was fed at a flow rate of 112 kg/h into the fluidized-bed reactor through a gas distributor disposed at a bottom of the fluidized-bed reactor, and the pressure of the fluidized-bed reactor was controlled at 9 atm.

Subsequently, ethanol which was heated to 155° C. and thereby vaporized was fed at a rate of 10 kg/h into the fluidized-bed reactor, and, further, CO and $O_2$ were fed with the feeding rate of nitrogen reduced so that the feeding rates of CO and $O_2$ were finally 112 kg/h and 9.6 kg/h, respectively, and the feeding of $N_2$ was discontinued.

Thereafter, a liquid ethanol heated to 80° C. was directly fed just above the gas distributor into the fluidized bed at a rate of 5 kg/h. The feeding rate of the liquid ethanol was gradually increased while the feeding rate of the vaporized ethanol was gradually decreased until all the ethanol became fed in liquid phase at a rate of 92 kg/h.

Under this condition, the reaction was continued for 6 hr. Throughout the reaction, cooling by passing 80° C. water through only two of the U-shaped cooling pipes enabled the desirable control of the reaction temperature at 140°±3° C.

The composition analysis and the flow rate measurement of the reactor effluent gas showed that the ethanol conversion was 27% and the diethyl carbonate (DEC) selectivity was 87%. The DEC yield determined from the material balance was 28 kg/h.

Comparative Example 3

The same fluidized-bed reactor as in Example 1 was used and the reaction pressure was controlled at 9 atm by nitrogen in the same manner as in Example 1.

Subsequently, ethanol which was heated to 155° C. and thereby vaporized, CO and $O_2$ were fed into the fluidized-bed reactor at respective rates of 10, 112 and 9.6 kg/h, and the feeding of nitrogen was discontinued. 80° C. water was initially passed through only two of the U-shaped cooling pipes, and, while gradually increasing the feeding rate of vaporized ethanol, the number of cooling pipes through which hot water was passed was increased. However, when the feeding rate of vaporized ethanol was increased to 60 kg/h, the reaction temperature continued to increase irrespective of the feeding of hot water to all the six cooling pipes with the result that the $CO_2$ concentration of the effluent gas exhibited a grave increase.

Therefore, the feeding rate of vaporized ethanol was decreased to 57 kg/h and the operation was continued for 6 hr.

The ethanol conversion, DEC selectivity and DEC yield were 26%, 87% and 17 kg/h, respectively.

It was found that the DEC yield of Example 5 was 1.6 times that of Comparative Example 3 and that the utility corresponding to 85% of the cooling duty and all the heat of vaporization of ethanol could be saved in Example 5 as compared with those of Comparative Example 3.

Example 6

Dimethyl carbonate was produced by the use of the apparatus shown in FIG. 4, which was not provided, however, with the gas recycle line 6a.

Six U-shaped cooling pipes each having an outside diameter of 34 mm and a length of straight line part of 1 m were inserted in a fluidized-bed reactor of 350 mm in diameter having a height of catalyst-packed bed of 1500 mm. Methanol was introduced in all the U-shaped cooling pipes.

Nitrogen heated to 140° C. was fed at a flow rate of 100 kg/h into the fluidized-bed reactor through a gas distributor disposed at a bottom of the fluidized-bed reactor, and the pressure of the fluidized-bed reactor was controlled at 9 atm. Subsequently, methanol which was heated to 140° C. and thereby vaporized was fed at a rate of 10 kg/h into the fluidized-bed reactor, and, further, CO containing 10 mol% of hydrogen and $O_2$ were fed with the feeding rate of nitrogen reduced so that, finally, the feeding rates of CO containing 10 mol% of hydrogen and $O_2$ were 144 kg/h and 8.2 kg/h, respectively, with the feeding of nitrogen discontinued.

Thereafter, pressurized liquid methanol was fed at a flow rate of 1200 kg/h to the cooling pipes. The methanol from the outlets of the cooling pipes was cooled to 90° C. by a heat exchanger 15 and fed to an upper part of an alcohol evaporator. The liquid methanol was withdrawn from the bottom thereof and recycled to the cooling pipes. The CO flow path which had supplied the fluidized-bed reactor with CO was switched so as to feed CO to the bottom of the alcohol evaporator, and the outlet gas of the alcohol evaporator was heated to 120° C. and fed into the fluidized-bed reactor.

Further, methanol was fed to the bottom of the alcohol evaporator while controlling the level of the liquid surface.

In the steady state, the alcohol supply and the temperature of the top of the evaporator were 54 kg/h and 85° C., respectively, and the cooling pipe inlet temperature, cooling pipe outlet temperature and supply temperature to evaporator of the methanol were 67° C., 101° C. and 90° C., respectively.

The composition analysis and the flow rate measurement of the reactor effluent gas showed that the methanol conversion was 30% and the DMC selectivity was 91%. The DMC yield determined from the material balance was 21 kg/h. The reaction temperature could appropriately be controlled at 145°±2° C.

The utility corresponding to 68% of the cooling duty and all the heat of vaporization of methanol during the steady-state operation could be saved in Example 6.

Example 7

Dimethyl carbonate was produced by the use of the apparatus shown in FIG. 5, which was not provided, however, with the gas recycle line 6a.

Six U-shaped cooling pipes each having an outside diameter of 34 mm and a length of straight line part of 1 m were inserted in a fluidized-bed reactor of 350 mm in diameter having a height of catalyst-packed bed of 1500 mm. Water was introduced in all the U-shaped cooling pipes.

Nitrogen heated to 140° C. was fed at a flow rate of 100 kg/h into the fluidized-bed reactor through a gas distributor disposed at a bottom of the fluidized-bed reactor, and the pressure of the fluidized-bed reactor was controlled at 9 atm. Subsequently, methanol which was heated to 140° C. and thereby vaporized was fed at a rate of 10 kg/h into the fluidized-bed reactor, and, further, CO containing 15 mol% of $CO_2$ and $O_2$ were fed with the feeding rate of $N_2$ reduced so that, finally, the feeding rates of CO containing 15 mol% of $CO_2$ and $O_2$ were 166 kg/h and 7.4 kg/h, respectively, with the feeding of $N_2$ discontinued.

Thereafter, methanol was recycled from the bottom of the alcohol evaporator to the top thereof at a flow rate of 1200 kg/h. Simultaneously, 79° C. water was fed at a flow rate of 1000 kg/h to the cooling pipes, and the hot water from the outlet thereof was cooled to 95° C. by means of a heat exchanger 18. The hot water was fed to a heat exchanger 19 attached to the alcohol evaporator in which the methanol was heated by the hot water. The CO flow path which had supplied the fluidized-bed reactor with CO was switched so as to feed CO to the bottom of the alcohol evaporator, and the outlet of the alcohol evaporator was heated to 120° C. and fed into the fluidized-bed reactor.

Further, methanol was fed to the bottom of the alcohol evaporator while controlling the level of the liquid surface.

In the steady state, the alcohol supply, the temperature of the evaporator top, the temperature of the evaporator bottom, the cooling pipe inlet temperature and the cooling pipe outlet temperature were 50 kg/h, 85° C., 68° C., 79° C. and 102° C., respectively.

The composition analysis and the flow rate measurement of the reactor effluent gas showed that the methanol conversion was 30% and the DMC selectivity was 90%. The DMC yield determined from the material balance was 19 kg/h.

The reaction temperature could appropriately be controlled at 145°±2° C.

The utility corresponding to 69% of the cooling duty and all the heat of vaporization of methanol during the steady-state operation could be saved in Example 7.

What is claimed is:

1. A process for producing a carbonic acid diester, which comprises carrying out a reaction in a vapor phase of an alcohol, carbon monoxide and oxygen in the presence of a catalyst in a fluidized-bed reactor so that an oxidative carbonylation of the alcohol occurs, thereby obtaining a carbonic acid diester, wherein a heat of reaction is removed by the latent heat of vaporization of the alcohol used as a raw material.

2. The process as claimed in claim 1, wherein at least part of the alcohol as a raw material is fed in liquid phase into a fluidized bed of the reactor.

3. The process as claimed in claim 1, wherein cooling pipes are provided in a fluidized bed of the reactor and at least part of the alcohol as a raw material is introduced in liquid phase into the cooling pipes so that at least part of the liquid alcohol is vaporized and then fed into the fluidized-bed reactor.

4. The process as claimed in claim 3, wherein carbon monoxide is introduced together with the liquid alcohol into the cooling pipes.

5. The process as claimed in claim 3, wherein cooling pipes in which water or an oil is introduced as a heat transfer medium are provided in a fluidized bed of the reactor.

6. The process as claimed in claim 1, wherein cooling pipes are provided in a fluidized bed of the reactor and the alcohol as a raw material is introduced in liquid phase thereinto as a heat transfer medium so that the liquid alcohol is heated to an increased temperature, the heated liquid alcohol is fed into an evaporator in which the liquid alcohol is mixed with carbon monoxide and at least part of the alcohol is vaporized, and the vaporized alcohol is fed together with the carbon monoxide into the fluidized-bed reactor.

7. The process as claimed in claim 1, wherein cooling pipes are provided in a fluidized bed of the reactor and water or an oil as a heat transfer medium is circulated therethrough, the obtained hot water or hot oil being passed through a heat exchanger to thereby effect a heat exchange between the hot water or oil and a liquid alcohol so that the liquid alcohol is heated to an increased temperature, the heated liquid alcohol is fed into an evaporator in which the liquid alcohol is mixed with carbon monoxide and at least part of the alcohol is vaporized, and the vaporized alcohol is fed together with the carbon monoxide into the fluidized-bed reactor.

\* \* \* \* \*

UNITED STATES PATENT AND TRADEMARK OFFICE
CERTIFICATE OF CORRECTION

PATENT NO. : 5,831,113
DATED : November 3, 1998
INVENTOR(S) : Umino et al.

It is certified that error appears in the above-identified patent and that said Letters Patent is hereby corrected as shown below:

Title Page, [57] ABSTRACT, Line 17 "there for" should read --therefor--.

Column 1, Line 37 after "producing" insert --a--.

Column 1, Line 56 replace "Wo" with --WO--.

Column 2, Line 10 replace "1700°C" with --170°C--.

Column 10, Line 66 replace "8° to 250°C" with --80° to 250°C-- .

Column 11, Line 27 before "(4)" should read --and (4) the--

Signed and Sealed this

Sixth Day of July, 1999

Attest:

Q. TODD DICKINSON

Attesting Officer

Acting Commissioner of Patents and Trademarks